United States Patent [19]
Futaki et al.

[11] 3,932,182
[45] Jan. 13, 1976

[54] AN ORGANIC PHOTOCONDUCTIVE COMPOSITION COMPRISING AN ORGANIC PHOTOCONDUCTIVE COMPOUND AND A SENSITIZING COMPOUND HAVING AN ACTIVE METHYLENE GROUP

[75] Inventors: Kiyoshi Futaki; Hirokazu Tsukahara; Kazuhiro Emoto, all of Kyoto, Japan

[73] Assignee: Mitsubishi Paper Mills, Ltd., Tokyo, Japan

[22] Filed: Jan. 17, 1974

[21] Appl. No.: 434,325

Related U.S. Application Data

[62] Division of Ser. No. 151,914, June 10, 1971, abandoned.

[30] Foreign Application Priority Data

June 10, 1970  Japan.................................. 45-50024

[52] U.S. Cl..................... 96/1.6; 96/1.5; 96/1.5 C; 260/257; 260/260; 260/306.7 T; 260/562 R
[51] Int. Cl.² .......................................... G03G 5/09
[58] Field of Search..................... 96/1.5, 1.6, 1.5 C; 252/501

[56] References Cited
UNITED STATES PATENTS

| | | | |
|---|---|---|---|
| 3,155,503 | 11/1964 | Cassiers et al.................... | 96/1.5 |
| 3,159,483 | 12/1964 | Behmenburg et al.............. | 96/1.5 X |
| 3,163,531 | 12/1964 | Schlesinger....................... | 96/1.5 X |
| 3,234,280 | 2/1966 | Fox et al............................ | 96/1.5 X |
| 3,287,114 | 11/1966 | Hoegl................................ | 96/1.5 X |
| 3,331,687 | 7/1967 | Kosche.............................. | 96/1.5 |
| 3,387,973 | 6/1968 | Fox et al............................ | 96/1.5 |
| 3,536,484 | 10/1970 | Dowden et al.................... | 96/1.5 |
| 3,877,937 | 4/1975 | Keller et al........................ | 96/1.6 |
| T889,022 | 8/1971 | Reynolds et al................... | 96/1.6 |

OTHER PUBLICATIONS

Chemical Abstracts (1), Vol. 66, 1967, p. 76575 z.
Chemical Abstracts (2), Vol. 68, 1968, p. 7935 h.

*Primary Examiner*—David Klein
*Assistant Examiner*—John R. Miller
*Attorney, Agent, or Firm*—Sughrue, Rothwell, Mion, Zinn & Macpeak

[57] ABSTRACT

An organic photoconductive composition, useful as an electrophotosensitizing material consisting of an organic photoconductive compound and a compound having an active methylene, as chemical sensitizer, represented by the formula,

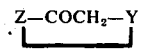

or

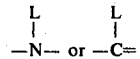

wherein R is a substituted or unsubstituted phenyl, alkyl, arylamino, alkylamino, aryloxy or alkoxy; X is acyl, carbamoyl, phenyl-substituted carbamoyl or cyano; Y is carbonyl, oxygen, sulfur, $$\underset{|}{-N-} \text{ or } \underset{|}{-C=}$$

(wherein L is hydrogen or alkyl); Z is a residue necessary to form a 5- or 6-membered ring, and method for making the same.

10 Claims, No Drawings

AN ORGANIC PHOTOCONDUCTIVE COMPOSITION COMPRISING AN ORGANIC PHOTOCONDUCTIVE COMPOUND AND A SENSITIZING COMPOUND HAVING AN ACTIVE METHYLENE GROUP

This is a division of application Ser. No. 151,914, filed June 10, 1971, now abandoned.

BACKGROUND OF THE INVENTION

As the hitherto known organic photoconductive compounds, there are both polymeric or non-polymeric photoconductive compounds. Examples of said polymeric organic photoconductive compounds among them include poly-N-vinylcarbazole, poly-N-vinylcarbazole derivatives, polyacenaphthylene and the like, and examples of said non-polymeric organic photoconductive compounds include various aromatic condensates, heterocyclic compounds, aromatic amines, such as, for example, anthracene, imidazolone derivatives, oxazole derivative, N,N,N',N'-tetraphenyl-p-phenylenediamine derivative, benzidine derivative and the like. The former may usually be applied directly or in a mixture with a desirable plasticizer, and the latter in a mixture with a desirable binder to a support to make a uniform and smooth, glassy sensitive layer.

It has been generally known that the incorporation of various kinds of dyes into the photoconductive compound layer, in the case where the photoconductive compound is sensitive to ultraviolet rays, induces a spectral sensitization and can give a sensitive layer having a sensitivity at a visible region, and that the addition of an electron accepting compound, in the case where the photoconductive compound used shows an electron donating property, converts to an electron transfer type compound and leads to its chemical sensitization.

Thus, for example, as spectrum sensitizers there are known dyes, such as, rhodamine B, rhodamine B extra, crystal violet, victoria blue-B, fuchsine, night blue and acridine orange, and pyrylium salt. And also as the chemical sensitizer, there are known quinones, such as, anthraquinone, 2-methylanthraquinone, 1-nitroanthraquinone, and tetracyanoethylene, tetracyanoquinodimethane, benzoic acid, p-chlorophenol, m-nitrophenol, cinnamic acid and the like.

An object of the present invention is to obtain a chemical sensitizer showing far more excellent sensitizing effect than that of the hitherto known ones in the field of the latter chemical sensitizers, and another object of the present invention is to obtain an organic photoconductive composition sensitized with said sensitizer.

SUMMARY OF INVENTION

As a result of many attempts, the inventors have found that a compound represented by the following formula,

R-CO-CH$_2$-X or

wherein R is a substituted or unsubstituted phenyl, alkyl, arylamino, alkylamino, aryloxy or alkoxy; X is acyl, carbamoyl, phenyl-substituted carbamoyl or cyano; Y is carbonyl, oxygen, sulfur,

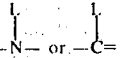

(wherein L is hydrogen or alkyl); Z is a residue necessary to form a 5- or 6-membered ring, namely, a straight chain compound or a compound forming a cyclic compound having an active methylene group at any position thereof exhibits excellent sensitizing activity, and have therein attained the present invention.

DETAILED DESCRIPTION OF THE INVENTION

The substituted phenyl group of R represented in the above formula includes ones substituted with halogen, nitro, alkoxy, carboxyl, and methyl.

The embodiments of aryl in arylamino group and aryloxy group of R include phenyl and naphthyl of which the benzene or naphthalene rings may be substituted with methyl, alkoxy, halogen, carboxyl, hydroxy, nitro and trifluoromethyl.

The desired examples of the alkoxy group of R are lower alkoxy groups of less than 5 carbon atoms. The acyl group in X includes a substituted or unsubstituted benzoyl group, which may be substituted with halogen, nitro and hydroxy.

Embodiments of the case where

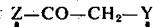

forms a 5- or 6-membered ring are pyrazolone, thiazolidone, oxazolidone, thiohydantoin, barbituric acid, thiobarbituric acid and their derivatives.

These compounds will be further described by the following embodiments, which are presented for illustrative rather than limitative purposes.

The typical examples of the straight chain compounds include malon-arylamides, such as, malon-dianilide, malon-bis-4-chloroanilide, malon-bis-4-bromoanilide, malon-bis-2,3-dichloroanilide, malon-bis-4-hydroxyanilide, malon-bis-3-carboxyanilide, malon-bis-3-methoxyanilide, malon-bis-3-methylanilide, malon-bis-N-methyldianilide, malon-bis-naphthylamide and the like; benzoylacetamide derivatives, such as, benzoylacetanilide, benzoylaceto (3-nitro) anilide, 3-chlorobenzoylaceto (3-nitro)anilide,α-(2-methoxybenzoyl) acetanilide,α-(4-methylbenzoyl) acetanilide 4-[α-(4- hexadecyloxy) benzoylacetamido] -phthalic acid dimethyl ester acetanilide, 3-nitrobenzoylaceto (3' -trifluoromethyl) anilide, benzoylaceto (2,5-dichloro) anilide, N-cyclohexyl-(4'-chlorobenzoyl) acetamide, N-methyl-(4-nitrobenzoyl) acetamide and the like; dibenzoylmethane derivatives, such as, 4-bromo-dibenzoylmethane, 2-nitrodibenzoylmethane, 4-chlorodibenzoylmethane, 2-hydroxy-dibenzoylmethane and the like; N, N' -bis-acetoacetyl-phenylenediamine, ethyl (4-nitrobenzoyl) acetate, (4-chloro-benzoyl) acetate, cyanoacetanilide, ω-cyanoacetophenone, N, -methyl-N'-phenylmalon-anilide, and its derivatives.

Typical examples of the cyclic compounds include barbituric acids and barbituric acid derivatives, such as, N,N'-diethyl-2-thiobarbituric acid, N,N'-diethyl-2-barbituric acid, N,N'-diphenyl-2-thiobarbituric acid, N,N'-bis (p-methylphenyl)-2-barbituric acid and the like; thiazolidone derivatives, such as, 3-(α-carboxymethyl)-4-thiazolidone-2-thione, 3-(β-oxyethyl)-2- phenyliminothiazolidone, 3-phenyl-4-thiazolidone-2-thione, 3-ethyl-4-thiazolidone-2-thione and the like; oxazolidone derivatives, such as 3-ethyl-4-oxazolidone-2-thione, 3-(α-carboxymethyl)-4-oxazolidone-2-thione, 3-phenyl-4-oxazolidone-2-thione and the like; thiohydantoin derivatives, such as, 3-ethylthiohydantoin, 1-phenyl-3-ethylthiohydantoin, 1,3-diethylthiohydantoin, 1,3-diphenylthiohydantoin and the like; pyrazolone derivatives, such as 1-phenyl-5-pyrazolone, 1-phenyl-3-methyl-5-pyrazolone, 1-phenyl-3-phenyl-5-pyrazolone and the like.

The additional quantity of these compounds having active methylene may be 1 to 50 parts by weight, preferably, 10 to 30 parts by weight per 100 parts by weight of the photoconductive compound.

In the practice of the present invention, there are employed all of the foregoing organic polymeric and non-polymeric photoconductive compounds which have hitherto been used as organic photoconductive compound, but the use of a non-polymeric compound as the photoconductive compound requires a desirable binder, for example, a synthetic condensation type polymer and addition polymerization type polymers, such as, polycarbonate, polysulfone, polystyrene, styrene-butadiene copolymers and the like, which may be preferably used in the proportion of 100 to 500 parts by weight, especially, 150 to 300 parts by weight, per 100 parts by weight of these photoconductive compounds.

The production of an electron photosensitive element may usually be conducted by applying a solution or dispersion of a compound containing active methylene, a binder resin, a photoconductive compound and a spectral sensitizer in a desired solvent selected from the groups consisting of chloroform, monochlorobenzene, and toluene to a support. The spectral sensitizer used herein may also be selected from the hitherto known ones, as described above, such as, for example, rhodamine B, rhodamine B extra, crystal violet, victoria blue-B, fuchsine, night blue, acridine orange, pyrylium salt and the like.

As the supports, there are used metal plates such as copper and aluminum, a surface-treated paper in which a solvent is hardly immersed, a synthetic resin film of which the intrinsic resistance is decreased to below $10^9 \Omega cm^{-1}$, preferably, below $10^5 \Omega cm^{-1}$ by using an antistatic agent, and a glass plate, paper or synthetic resin film laminated with a metal, or a metal oxide and/or a metal halide by an evaporation process. The practical application thereof can easily be accomplished by a rotary applying method, a casting method and a doctor blade method. In the practice of producing the same, the preferred thickness of said sensitive layer may be 3 to 20μ.

The generally popular production of an electron photographic image using the photosensitive element made by the foregoing methods may be achieved in a conventional electron photographic method. For example, by treating the sensitive layer several times with a corona discharge apparatus applied with +6 KV in a dark place, the positive charge is accumulated on the surface of said sensitive layer and the potential becomes 300 to 900 V. And on the other hand, the reversion of position of the applied surface makes it possible to accumulate a negative charge on the surface of said sensitive layer. On irradiating the sensitive layer with a proper light source, for example, tungsten electric bulb through a positive pattern, the charge on the exposed portion is removed, and on applying successively the sensitive layer with a negatively charged developer powder, which has been broadly known as toner, it gives a positive image in the case where the charge on the surface of said sensitive layer is positive, and reversely, a negative image in the case where the charge on the surface thereof is negative. The easy fixation can be effected by either heating it weakly, or passing it through a proper solvent vapor. Also, development can be conducted using a liquid development system, instead of a dry toner.

Several syntheses of the typical compounds having an active methylene used effectively in the present invention will be more particularly illustrated as follows:

SYNTHESIS EXAMPLE 1

α-(4-nitrobenzoyl)aceto(2-methoxy)anilide

12.3 g of o-anisidine and 26.1 g of p-nitrobenzoylacetoacetic acid ethyl ester were dissolved in 400 ml of xylene, heated under reflux for 6 hours. Thereafter, the solution was allowed to stand at room temperature overnight and cooled, and the formed crude crystals were filtered off. By recrystallizing it from 250 ml of ethyl acetate, 9.5 g of white crystals (m.p. 136.5° to 138.0°C) were obtained.

SYNTHESIS EXAMPLE 2

Malon-bis-3-nitroanilide

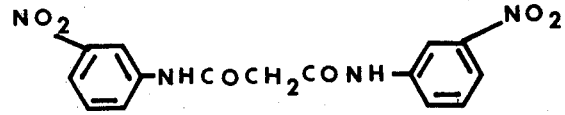

13.8 g of 3-nitroaniline and 8.1 g of diethyl malonate were heated on an oil bath (bath temperature: 190°–195°C) while stirring for 2 hours and cooled up to room temperature. After adding 100 ml of methanol thereto and ice-cooling thereof, the crude crystals thus formed were filtered off. By recrystallizing it from 200 ml of ethyl acetate, 21 g of white needle crystals (m.p. 195° to 196°C) were obtained.

SYNTHESIS EXAMPLE 3

N,N'-diethyl-2-thiobarbituric acid

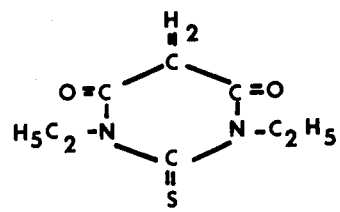

120 g of N,N'-diethyl-thiourea and 132.0 g of diethyl malonate were placed in a solution of 4.6 g of metallic sodium in 64 ml of anhydrous alcohol and heated on an oil bath (bath temperature: 100°- 105°C) while stirring for 50 hours. A great quantity of white precipitate was formed in accordance with performance of the reaction. After cooling the reaction mixture up to room temperature, the precipitate was dissolved on adding 62 ml of water thereto, and then ethanol was removed by distillation. The residual jelly like material was mixed with 40 ml of water to dissolve it. When said solution was placed in 100 ml of 6 N-hydrochloric acid solution, the mixture gave immediately a brownish powdered crystal. Then, the resultant mixture was cooled in ice water and the powder was filtered off, and washed with water until the filtrate became neutral and finally was recrystallized from ethanol to obtain 15.8 g of white needle crystals (m.p. 103.0° to 103.5°C).

SYNTHESIS EXAMPLE 4

3-($\beta$-hydroxyethyl)-2-phenyliminothiazolidone

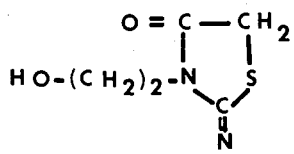

10 g of N-hydroxyethylamine was dissolved in 10 ml of water, and 24 g of phenylisothiocyanate was dropped therein within 1 minute at an ordinary temperature. Thereafter, the resultant mixture was heated on a water bath for 3 minutes, cooled and the precipitated crystals were filtered off. By recrystallizing it from 200 ml of methanol, 26.5 g of N-hydroxyethyl-N'-phenylthiourea having m.p. of 137.5° to 139.5°C was given. 1.96 g of the so obtained N-hydroxyethyl-N-phenylthiourea and 1.23 g of ethylchloroacetate were dissolved in ethanol and heated on a water bath under reflux for 1 hour. The reaction mixture was ice-cooled, poured into 30 ml of ice water and allowed to stand overnight, and then the white solid formed was taken out. By recrystallizing it from 8 ml of benzene, 0.9 g of the objective material having m.p. of 8.40° to 8.7°C was obtained.

The sensitivities between the hitherto known chemical sensitizer and these chemical sensitizers containing active methylene groups were compared and resulted in the following table.

The designation of sensitivity is illustrated as amount of light required for a half decay of the surface potential E-½ (lux. second), and it can be recognized that the smaller the number is, the more effective it becomes.

In addition to that, there were used a tungsten electric bulb as the light source, crystal violet as the spectral sensitizer and polystyrene as the binder.

TABLE 1

| Compound (A) | (Organic photoconductive compound: N,N,N',N'-tetrabenzyl-m-phenylenediamine) | | | |
|---|---|---|---|---|
| | E-½ (lux.sec) | Compound (B) | | E-½ (lux.sec) |
| Malon-di-anilide | (5) | 200 | 2-Methylanthraquinone | 3000 |
| | | | (10) | |
| Malon-bis-1,3-dichloro-anilide | (10) | 125 | Anthraquinone | (10) | 3000 |
| Benzoylacetanilide | (10) | 150 | Trichloroacetic acid | (15) | 750 |
| Dibenzoylmethane | (10) | 100 | Dichloroacetic acid | (15) | 1500 |
| 4-Chlorodibenzoyl-methane | (15) | 100 | Bromanil | (10) | 600 |
| | | | 4-Chlorophenol | (10) | 700 |
| N,N'-diethyl-2-thio-barbituric acid | (15) | 85 | Cinnamic acid | (10) | 2500 |
| N,N'-dimethyl-2-barbituric acid | (15) | 150 | Picric acid | (3) | 3500 |
| | | | Phthalic acid | (5) | 4000 |
| 1-Phenyl-5-pyrazolone | (10) | 200 | Acetanilide | (10) | 4000 |

TABLE 2

| Compound (A) | (Organic photoconductive compound: N,N,N',N'-tetraphenyl-p-xylenediamine) | | | |
|---|---|---|---|---|
| | E-½ (lux. sec) | Compound (B) | | E-½ (lux. sec) |
| 3-phenyl-4-thia-zolidone-2-thion | (20) | 110 | Hydrous chloral | (10) | 800 |
| Malon-bis-3-nitro-anilide | (15) | 90 | o-nitrophenol | (10) | 4000 |
| N-methyl-N-phenyl malonanilide | (10) | 125 | Crotonic acid | (10) | 3800 |
| 1,3-diethylthio-hydantoin | (15) | 250 | Benzoic acid | (10) | 3000 |
| N,N'bis-acetoacetyl-phenylenediamine | (15) | 450 | Chloranil | (10) | 3700 |
| 2-$\beta$-hydroxyethyl-2-phenyliminothiazolidone | (15) | 200 | | | |

The compound (A) is a chemical sensitizer according to the present invention, and the compound (B) is a conventional known one. The added quantity of them is 10 to 30 parts by weight per 100 parts by weight of the photoconductive compound. In addition, numbers in the parentheses on Tables 1 and 2 designate the added quantity (part by weight) per each 100 parts by weight of photoconductive compound. The compounds having active methylene groups exhibit excellent sensitizing activity to other photoconductive compounds, such as, poly-N-vinylcarbazole.

The following examples will serve to set forth more specifically the present invention without limiting it to the examples themselves.

EXAMPLE 1

1 g of N,N,N',N'-tetraphenyl-p-phenylenediamine, 2 g of polystyrene resin, 0.002 g of crystal violet and 0.2 g of benzoyl acetanilide were dissolved in 25 ml of chloroform, and applied onto an aluminum plate to make a sensitive layer having 5μ in thickness by means of a rotary applying method.

The aluminum plate was charged positively by a corona discharge apparatus applied with 6 KV in a conventional way. By applying a powdered carbon charged negatively to the aluminum plate, after exposing it under a positive original at 500 lux for 2 seconds by means of 100 W glow lamp as the light source, an image about in contrast similar closely to the original was given. Finally, the fixation was conducted by heating it weakly.

Without the addition of benzoyl acetanilide thereto, there was given no clear image even when it was exposed at 500 lux for 5 seconds.

EXAMPLE 2

1 g of N,N,N',N'-tetrabenzyl-m-phenylenediamine, 2 g of polycarbonate resin, 0.001 g of victoria blue-B, and 0.1 g of malon-bis-1,3-dichloroanilide were dissolved in 25 ml of chloroform and applied onto a surface-treated paper to form a sensitive layer having 6μ in thickness by means of a doctor blade method. The resultant paper was charged positively by a corona discharge apparatus in the same manner as in Example 1, and by applying a powdered carbon charged negatively to the paper, after exposing it under a positive original at 500 lux for 2.5 seconds, an image about in contrast similar closely to the original was given. And the fixation was conducted by heating it weakly. Without the addition of malon-bis-1,3-dichloroanilide thereto, there was given no clear image even when it was exposed at 500 lux for 10 seconds.

EXAMPLE 3

1 g of 3,3'-dichlorobenzidine, 2 g of styrene-butadiene copolymer resin, 0.002 g of night blue and 0.2 g of malon-bis-3-nitroanilide were dissolved in 25 g of monochlorobenzene-chloroform mixture, and the solution was applied to a surface-treated paper to form a sensitive layer having 6μ thickness by means of a doctor blade method. In the same manner as in Example 1, a clear image was given. Without the addition of malon-bis-3-nitroanilide, there was given no clear image even when it was exposed at 500 lux for 10 seconds.

EXAMPLE 4

1 g of N,N,N',N'-tetrabenzyl-m-phenylene-diamine, 2.5 g of polysulfone resin, 0.001 g of crystal violet, and 0.2 g of N,N'-diethyl-2-barbituric acid were dissolved in 20 g of chloroform, and the solution was applied to a surface-treated paper to form a sensitive layer having 4μ in thickness by means of a doctor blade method. The paper was charged positively by a corona discharge apparatus, and after exposure thereof under a positive original at 500 lux for 0.5 seconds, the development with a liquid developer toner gave an image about in contrast similar closely to the original. Finally, the fixation thereof was conducted by heating it weakly. Without the addition of N,N'-diethyl-2-barbituric acid, there was given no clear image even when it was exposed at 500 lux for 5 seconds.

EXAMPLE 5

1 g of poly-N-vinylcarbazole, 0.2 g of N,N'-diethyl-2-thiobarbituric acid, and 0.001 g of crystal violet were dissolved in 30 g of monochlorobenzene, and the solution was applied to an alumina plate by means of a casting method. The plate was charged positively by means of a corona discharge apparatus in a conventional way, and after exposure thereof under a positive original at 500 lux for 1 second, the development with a liquid developer toner gave an image about in contrast similar closely to the original.

Finally, the fixation thereof was conducted by heating it weakly. Without the addition of N,N'-diethyl-2-thiobarbituric acid thereto, there was given no clear image even when it was exposed at 500 lux for 1 second.

EXAMPLE 6

1 g of N,N,N',N'-tetrabenzyl-m-phenylenediamine, 1.5 g of polystyrene 1.25 × 10⁻³ g of victoria blue-B and 0.1 g of 3-(β-hydroxyethyl)-2-phenyliminothiazolidone were dissolved in 25 g of toluene, and the solution was applied to an alumina plate to form a sensitive layer having 5μ in thickness by means of a casting method. The resultant plate was charged positively by means of a corona charge apparatus in a conventional way, and exposed under a positive original. And the development with a wet toner gave a clear visible image. The exposing quantity at that time was 500 lux for 1 second. Without the addition of 3-(β-hydroxyethyl)-2-phenyliminothazolidone, there was given no clear image even when it was exposed at 500 lux for 5 seconds.

EXAMPLE 7

1 g of N,N,N',N'-tetraphenyl-m-xylenediamine, 2 g of polystyrene (degree of polymerization: 1.25 × 10²), 15 g of crystal violet and 0.1 g of 3-phenyl-4-oxazolidone-2-thione were dissolved in 15 g of toluene, and the solution was applied to a surface-treated paper to form a sensitive layer having 5μ in thickness by means of a doctor blade method. The resultant paper was treated in the same manner as in Example 6 and as the result, a visible image was given. The exposing quantity at that time was 500 lux for 1 second. Without the addition of 3-phenyl-4-oxazolidone-2-thione, there was given no clear image.

What is claimed is:

1. An organic photoconductive composition comprising an organic photoconductive compound and a sensitizing compound having an active methylene group represented by the formula

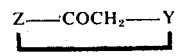

wherein Y is a carbonyl group, oxygen, sulfur,

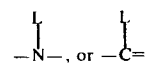

(wherein L is a hydrogen or an alkyl group); Z is a residue necessary to form 5- or 6-membered ring; said sensitizing compound being present in an amount of 1 to 50 parts by weight per 100 parts by weight of said organic photoconductive compound.

2. An organic photoconductive composition comprising an organic photoconductive compound and a compound having an active methylene group represented by the formula,

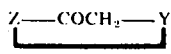

wherein Z and Y are a residue necessary to form pyrazolone ring, thiazolidone ring, oxazolidone ring, thiohydantoin ring, barbituric ring, and thiobarbituric ring together with the $COCH_2$ group.

3. A composition as claimed in claim 1, wherein said compound having an active methylene group is N, N'-diethyl-2-barbituric acid.

4. A composition as claimed in claim 1, wherein said compound having an active methylene group is N, N'-diethyl-2-thiobarbituric acid.

5. A composition as claimed in claim 1, wherein said compound having an active methylene group is 3-phenyl-4-oxazolidone-2-thione.

6. A composition as claimed in claim 1, wherein said organic photoconductive compound is N, N, N', N'-tetraphenyl-p-phenylenediamine.

7. A composition as claimed in claim 1, wherein said organic photoconductive compound is N, N, N', N'-tetrabenzyl-m-phenylenediamine.

8. A composition as claimed in claim 1, wherein said organic photoconductive compound is benzidine or its derivative.

9. A composition as claimed in claim 1, wherein said organic photoconductive compound is poly-N-vinyl carbazole.

10. A composition as claimed in claim 1, wherein said organic photoconductive compound is N, N, N', N'-tetraphenyl n-xylydendiamine.

* * * * *